United States Patent [19]

Lindberg et al.

[11] 4,237,311
[45] Dec. 2, 1980

[54] 2-METHYL-1-(SUBSTITUTED)PHENYL-2-PROPYL ESTERS OF 2-AMINOPROPANOIC ACID

[75] Inventors: Ulf M. A. Lindberg; Svante B. Ross, both of Södertälje; Seth-Olov Thorberg, Järna; Sven O. Ö gren, Södertälje, all of Sweden

[73] Assignee: Astra Läkemedel Aktiebolag, Södertalje, Sweden

[21] Appl. No.: 932,669

[22] Filed: Aug. 10, 1978

Related U.S. Application Data

[63] Continuation of Ser. No. 757,484, Jan. 6, 1977, abandoned, which is a continuation-in-part of Ser. No. 554,497, Mar. 3, 1975, abandoned.

[30] Foreign Application Priority Data

Mar. 11, 1974 [SE] Sweden .................. 7403176

[51] Int. Cl.³ .................. C07C 101/19; A61K 31/22
[52] U.S. Cl. .................. 560/173; 424/311; 560/228
[58] Field of Search .................. 560/173

[56] References Cited

U.S. PATENT DOCUMENTS

| | | | |
|---|---|---|---|
| 2,370,015 | 2/1945 | Dahner | 260/471 |
| 2,417,773 | 3/1947 | Martin | 260/482 R |
| 2,543,764 | 3/1951 | Cusic | 260/482 R |
| 3,317,584 | 5/1967 | Stoffel | 260/482 R |
| 3,541,135 | 11/1970 | Johl | 260/471 |

FOREIGN PATENT DOCUMENTS 2507429  9/1975  Fed. Rep. of Germany ...... 260/482 R
46-2502  1/1971  Japan ............................. 260/482 R

OTHER PUBLICATIONS

Weil, Chemische Zentralblatt, pp. 208–209 (1924).
Lakner, Chemische Zentrablatt, pp. 1464–1465 (1930).
Allinger, "Organic Chemistry," pp. 528–529 (1971).

*Primary Examiner*—Natalie Trousof
*Assistant Examiner*—Michael Shippen
*Attorney, Agent, or Firm*—Brumbaugh, Graves, Donohue & Raymond

[57] ABSTRACT

A compound of the general formula

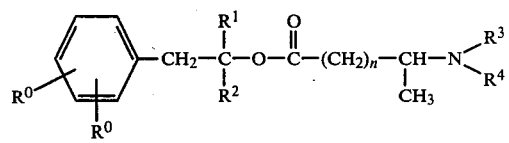

and pharmaceutically acceptable salts thereof, in which formula the groups $R^o$ are the same or different and are selected from the group consisting of hydrogen, halogen, alkyl having 1, 2 or 3 carbon atoms, and alkoxy having 1, 2 or 3 carbon atoms; $R^1$ is hydrogen, methyl or ethyl; $R^2$ is methyl or ethyl; $R^3$ and $R^4$ are the same or different and are hydrogen or an alkyl group having 1, 2 or 3 carbon atoms; and n is 0, 1 or 2. Pharmaceutical preparations containing these compounds are useful for treatment of depressive disorders.

5 Claims, No Drawings

2-METHYL-1-(SUBSTITUTED)PHENYL-2-PROPYL ESTERS OF 2-AMINOPROPANOIC ACID

This is a continuation of application Ser. No. 757,484, filed Jan. 6, 1977, now abandoned; which is a continuation-in-part of our copending application Ser. No. 554 497/75 filed Mar. 3, 1975 now abandoned.

This invention relates to new aralkyl esters of aminoacids, and processes for their preparation. This invention also relates to methods for the pharmacological use of these compounds and to pharmaceutical preparations containing such compounds.

An object of this invention is to provide compounds having effect on the central nervous system in man, especially antidepressive activity, and having a reduced frequency of side effects and increased effectiveness compared to drugs presently used in this area.

A further object of this invention is to provide pharmaceutical preparations containing as active ingredient a compound according to this invention.

Still an object of this invention is to provide methods for the treatment of depressive disorders in man, by selectively inhibiting the central neuronal uptake of 5-hydroxytryptamine.

The presently most used compound for controlling depressions in man is imipramine (Tofranil ®)

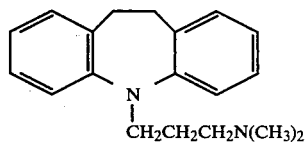

This compound is both mood elevating and psychomotor activating, but it possesses several disadvantages. It is anticholinergic and causes anticholinergic symptoms such as dryness of the mouth, tremor, tachycardia and sweating. In higher doses it can provoke serious heart arrhythmias and in normal doses it can cause toxic interactions in persons with heart failures. Furthermore, another drawback with treatment with imipramine is the late onset of the antidepressive effect, which effect is observable first after about 3 weeks of treatment.

It has been shown that imipramine has an effect on the action of the transmitter substances in the central nervous system. More specifically, imipramine inhibits the re-uptake mechanism of noradrenaline (NA) and 5-hydroxytryptamine (5-HT). The mood elevation part of the antidepressive action is assumed to be mainly related to the inhibition of 5-HT uptake.

According to the present invention we have found that certain new compounds, which can be described as aralkyl esters of amino acids, can be used for inhibiting selectively the central neuronal uptake of 5-hydroxytryptamine. Further the heart toxicities for these new compounds are considerably weaker than those of imipramine.

The new compounds according to the invention can be described by the general formula

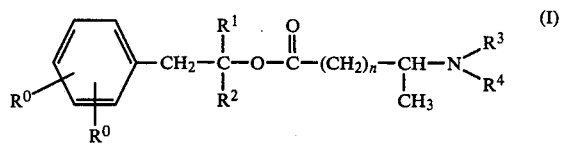

in which formula the groups $R^o$ are the same or different and are selected from the group consisting of hydrogen, halogen, alkyl having 1, 2 or 3 carbon atoms, and alkoxy having 1, 2 or 3 carbon atoms; $R^1$ and $R^2$ are methyl $R^3$ and $R^4$ are the same or different and are hydrogen or an alkyl group having 1, 2 or 3 carbon atoms: n is 0, including pharmaceutically acceptable acid-addition salts thereof.

Since these new compounds contain at least one asymmetric carbon atom, they exist in the form of optically active forms, and can be resolved into their optical antipodes by well known methods such as by using optically active acids such as tartaric acid, camphor-10-sulphonic acid, dibenzoyl tartaric acid, and the like.

A preferred subgroup of compounds within the invention is obtained when, in the formula I above, the groups $R^o$ are the same or different and are selected from halogen, alkyl with 1-3 carbon atoms and alkoxy with 1-3 carbon atoms, preferably selected from halogen and methyl. Further another preferred subgroup of compounds within the invention is obtained when, in the formula I above, $R^1$ and $R^2$ are methyl and n is 0, or $R^1$ and $R^2$ are methyl, n is 0 and $R^3$ and $R^4$ are hydrogen.

A particularly preferred subgroup of compounds within the invention is obtained when, in the formula I above, the groups $R^o$ are selected from halogen, methyl and hydrogen; the groups $R^1$ and $R^2$ are methyl; n is 0; and the groups $R^3$ and $R^4$ are the same or different and are selected from hydrogen and an alkyl group having 1, 2 or 3 carbon atoms. Preferred subgroups within this group are obtained when not more than one of the groups $R^o$ is hydrogen, or when $R^3$ and $R^4$ are hydrogen, or when, simultaneously, not more than one of the groups $R^o$ is hydrogen and $R^3$ and $R^4$ are hydrogen.

The compounds of the following formulas can be mentioned as examples of compounds included in the invention:

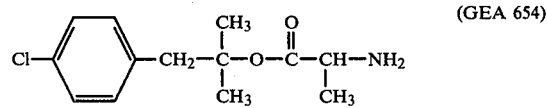
(GEA 654)

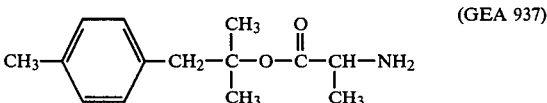
(GEA 937)

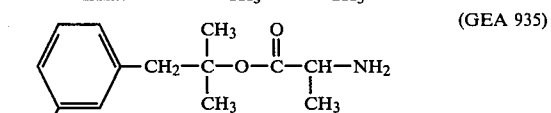
(GEA 935)

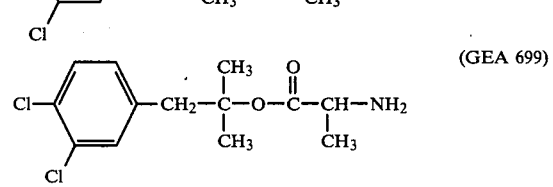
(GEA 699)

-continued

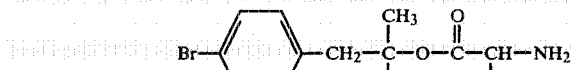 (GEA 917)

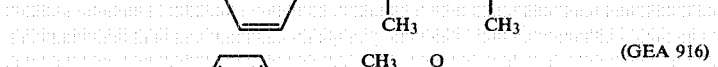 (GEA 916)

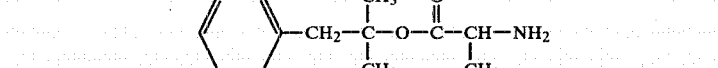 (GEA 953)

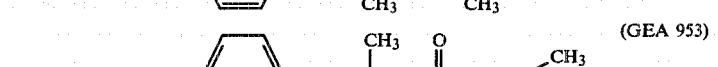 (GEA 822)

The compounds of the present invention may be prepared by
(a) reacting a compound of the formula

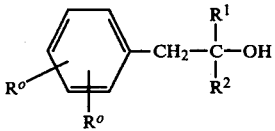 (II)

with an amine of the formula

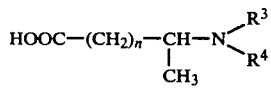 (III)

in which formulas $R^o$, $R^1$, $R^2$, $R^3$, $R^4$ and n are defined as above and X is halogen (such as chlorine, bromine or iodine) or p-toluene-sulphonyloxy; or
(b) reacting an alcohol of the formula

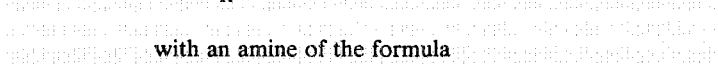 (IV)

with an amino acid, or derivative thereof, of the formula

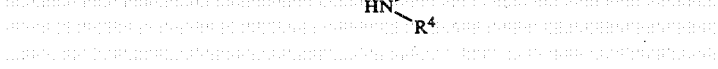 (V)

or with an amino acid derivative of the formula

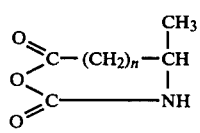 (VI)

in which formulas $R^o$, $R^1$, $R^2$, $R^3$, $R^4$ and n are defined as above.

The method (a) above is the preferred method for the preparation of the compounds according to the invention.

The intermediate of the formula II in method (a) is a new compound. Said compound may e.g. be prepared by reacting an alcohol of the formula IV above, with a compound of the formula

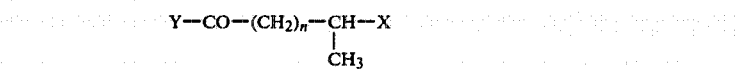

in which formula n and X are defined as above and Y is bromine or chlorine.

The reactions according to both method (a) and (b) are preferably conducted in an inert organic solvent capable of dissolving the reactants. Any suitable pressure and reaction temperature can be used. Preferably, the reactions are carried out under atmospheric or superatmospheric pressure, at a temperature of between −10 to +100° C., preferably between 0°–30° C.

The reaction according to method (b) is preferably conducted in the presence of dry hydrogen chloride as a catalyst. The starting materials of this reaction, i.e. the compounds of the formulas IV and V or VI are known and can be prepared according to methods known per se. For example, the compound of the formula VI can be prepared by reacting phosgene with the appropriate amino acid, optionally an optically active amino acid when an optically active modification of the end product of the formula I is desired.

The new compounds of this invention may be used therapeutically as the racemic mixtures of (+)- and (−)-forms, which in the usual case are obtained at the synthesis. They may also be resolved by methods known per se into the corresponding optically active modifications which, likewise, may be used in therapy. If desired, the optically active modification may be prepared by way of direct synthesis, e.g. via an optically active compound of the formula VI as described above.

PHARMACEUTICAL PREPARATIONS

In clinical practice the compounds of the present invention will normally be administered orally, rectally or by injection, in the form of pharmaceutical preparations comprising the active ingredient either as a free base or as a pharmaceutically acceptable non-toxic, acid addition salt, e.g. the hydrochloride, hydrobromide, lactate, acetate, phosphate, sulphate, sulphamate, citrate, tartrate, oxalate and the like in association with a pharmaceutically acceptable carrier. Accordingly, terms relating to the novel compounds of this invention whether generically or specifically are intended to include both the free amine base and the acid addition salts of the free base, unless the context in which such terms are used, e.g. in the specific examples would be inconsistent with the broad concept. The carrier may be a solid, semisolid or liquid diluent or capsule. These pharmaceutical preparations constitute a further aspect of this invention. Usually the active substance will constitute between 0.1 and 99% by weight of the preparation, more specifically between 0.5 and 20% by weight for preparations intended for injection and between 0.2 and 50% by weight for preparations suitable for oral administration.

To produce pharmaceutical preparations containing a compound of the invention in the form of dosage units for oral application the selected compound may be mixed with a solid pulverulent carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol waxes, and the like, and then compressed to form tablets. If coated tablets are required, the cores, prepared as described above, may be coated with a concentrated sugar solution which may contain, e.g. gum arabic, gelatine, talcum, titanium dioxide, and the like. Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compounds.

For the preparation of soft gelatine capsules (pearl-shaped closed capsules) consisting of gelatine and for example, glycerol or similar closed capsules, the active substance may be admixed with a vegetable oil. Hard gelatine capsules may contain granulates of the active substance in combination with solid, pulverulent carriers such as lactose, saccharose, sorbitol, mannitol, starches (e.g. potato starch, corn starch or amylopectin), cellulose derivatives or gelatine.

Dosage units for rectal application can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example, solutions containing from about 0.2% to about 20% by weight of the active substance herein described, the balance being sugar and a mixture of ethanol, water, glycerol, and propyleneglycol. Optionally such liquid preparations may contain colouring agents, flavouring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

Suitable daily doses of the compounds of the invention at therapeutical treatment of humans is 100 to 500 mg at peroral administration and 20 to 100 mg at parenteral administration.

The preferred compound of the invention has the formula

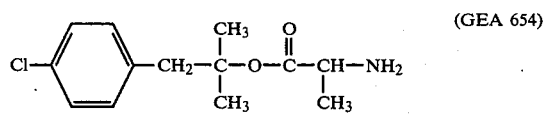

(GEA 654)

Preferably this compound is prepared and used in the form of its hydrochloride salt.

The preparation of some starting materials used for the preparation of compounds according to the invention is illustrated by the following examples 1–5.

EXAMPLE 1.

Preparation of 2-bromopropanoic acid 1-(4-chlorophenyl)-2-methyl-2-propylester used as starting material A solution of 4-chlorobenzyl chloride (165 g; 1.02 mole) in ether (500 ml) was added dropwise during one hour to magnesium (24.3 g; 1.00 mole) in a three-necked flask equipped with stirrer and reflux condenser. The spontaneous reflux was allowed to continue for another hour and the solution was cooled. Acetone (60.0 g, 1.30 mole) was added dropwise and the solution heated to reflux for three hours. After cooling, the reaction mixture was poured out on ice (500 ml) and concentrated hydrochloric acid (92 ml). The phases were separated. The organic phase was washed with water, dried ($Na_2SO_4$) and evaporated in vacuum. The residual oil was fractionated affording 1-(4-chlorophenyl)-2-methyl-2-propanol (b.p. 123°–124° C./12 mm Hg; $n_D^{25} = 1.5300$; 128.5 g, 70% yield).

The substituted propanol above (10.0 g, 54.2 mmole) was mixed with dimethylaniline (6.7 g, 55.3 mmole) and ether (25 ml). The solution was cooled and α-bromopropionyl bromide (11.6 g, 53.7 mmole) was added dropwise during 40 minutes. Stirring at room temperature for four hours gave a crystalline precipitate of dimethylaniline hydrochloride. Water (25 ml) was added to the reaction mixture. The phases were separated. The organic phase was washed with 5% sulphuric acid, saturated sodium hydrogen carbonate solution and water. The ether solution was dried ($Na_2SO_4$) and evaporated in vacuum. The residual oil was fractionated affording 2-bromopropanoic acid 1-(4-chlorophenyl)-2-methyl-2-propylester (b.p. 105°–115° C./0.15 mm Hg; 11.6 g, 60% yield).

EXAMPLE 2.

Preparation of 2-bromopropanoic acid 1-(3,4-dichlorophenyl)-2-methyl-2-propylester used as starting material A solution of 3,4-dichlorobenzylchloride (49.2 g, 0.254 mole) in dry ether (125 ml) was added dropwise during one hour to magnesium (6.08 g, 0.250 mole) in a three-necked flask equipped with stirrer and reflux condenser. Refluxing was continued until all the magnesium was dissolved and the solution was then cooled. Acetone (15.0 g, 0.258 mole) was added dropwise and the solution heated to reflux for three hours. After cooling the reaction mixture was poured out on ice (125 ml) and concentrated hydrochloric acid (23 ml). The phases were separated and the organic layer was washed with water, dried ($Na_2SO_4$) and evaporated in vacuum. The residual oil was distilled affording 1-(3,4-dichlorophenyl)-2-methyl-2-propanol (bp. 81°–83° C./0.2 mm Hg; 31.3 g, 57% yield). After several recrystallizations from petroleum ether the compound melted at 40°–41° C. The substituted propanol above (21.9 g, 0.100 mole) was mixed with dimethylaniline (12.4 g, 0.102 mole) and ether (50 ml). The solution was cooled and α-bromopropionyl bromide (21.4 g, 0.099 mole) was added dropwise during 40 minutes. Stirring at room temperature for 48 hours gave a crystalline precipitate of dimethylaniline hydrobromide, which was filtered off and washed with ether. The etheral solutions were combined and evaporated in vacuo. The residual oil was distilled affording 2-bromopropanoic acid 1-(3,4- dichlorophenyl)-2-methyl-2-propylester (bp. 135°–143° C./0.2 mm Hg; 19.2 g, 55% yield).

EXAMPLE 3.

Preparation of 2-bromopropanoic acid 2-methyl-1-phenyl-2-propylester used as starting material This compound (bp. 78° C./0.1 mm Hg; $n_D^{20}=1.5147$) was prepared in analogy with the method described in Example 1, using the compound 2-methyl-1-phenyl-2-propanol (bp. 93° C./12 mm Hg) as a starting material. The yield was 63%.

EXAMPLE 4.

Preparation of 2-bromopropanoic acid 1-(4-bromophenyl)-2-methyl-2-propylester used as starting material This compound was prepared in analogy with the method described in Example 1, using the compound 1-(4-bromophenyl)-2-methyl-2-propanol (bp. 98°–100° C./0.16 mm Hg; mp. 34°–35° C.) as starting material. The obtained product was purified by column chromatography (silica gel, benzene). Thin layer chromatography (silica gel, benzene): $R_f=0.72$.

EXAMPLE 6.

Preparation of 2-aminopropanoic acid 1-(4-chlorophenyl)-2-methyl-2-propylester

The ester (7.5 g, 23.5 mmole) obtained according to Example 1, was dissolved in ethanol (200 ml) and was cooled to 0° C. The solution was saturated with ammonia (4hours). Stirring was continued at room temperature for 24 hours. The solvent was removed under vacuum. The residual oil was dissolved in ether (250 ml) and the solution was extracted with 0.5 N hydrochloric acid. The acidic phase was made alkaline by the addition of concentrated ammonia. The alkaline phase was extracted twice with ether. The organic layer was dried ($Na_2SO_4$) and the solvent evaporated. From the basic oily residue the hydrochloride was prepared. Recrystallization from chloroform-ether afforded 2-aminopropanoic acid 1-(4-chlorophenyl)-2-methyl-2-propylester hydrochloride (mp. 123°–124° C., 5.1 g, 70% yield).

EXAMPLE 7.

Preparation of 2-aminopropanoic acid 1-(3,4-dichlorophenyl)-2-methyl-2-propylester The ester (8.85 g, 25.0 mmole) obtained according to Example 2, was dissolved in ethanol (350 ml) and cooled to 0° C. The solution was saturated with ammonia (3 hours). Stirring was continued at room temperature for 27 hours. The solvent was removed under vacuum. The residual oil was dissolved in ether (250 ml) and the solution was extracted with 1N hydrochloric acid. Cooling of the acidic phase afforded a crystalline precipitate which was filtered off, washed with ether and dried. Recrystallization from chloroform-ether afforded 2-aminopropanoic acid 1-(3,4-dichlorophenyl)-2-methyl-2-propylester hydrobromide (mp. 135°–136° C., 3.4 g, 42% yield).

EXAMPLE 8.

Preparation of 2-aminopropanoic acid 2-methyl-1-phenyl-2-propylester

This compound was prepared in analogy with the method described in Example 6, using the compound prepared according to Example 3 as a starting material. The desired product was recrystallized from acetone affording 2-aminopropanoic acid 2-methyl-1-phenyl-2-propylester hydrochloride (m.p 132°–133° C., 45% yield).

EXAMPLE 9.

Preparation of 2-aminopropanoic acid 1-(4-bromophenyl)-2-methyl-2-propylester

This compound was prepared in analogy with the method described in Example 6, using the compound prepared according to Example 4 as a starting material. The latter compound was thus reacted with ammonia, and after removal of the solvent the residual oil was dissolved in ether. By cooling the ether solution, the desired product was obtained as a white precipitate, which was recrystallized from acetone-isopropanol affording 2-aminopropanoic acid 1-(4-bromophenyl)-2-methyl-2-propylester hydrobromide (mp. 147°–148° C., 27% yield).

EXAMPLE 10.

Preparation of 2-dimethylaminopropanoic acid 1-(4-chlorophenyl)-2-methyl-2-propylester The ester (10 g, 0.0313 mol) obtained according to Example 1 was mixed with benzene (30 ml) and dimethylamine (5.62 g, 0.125 mole). The mixture was transferred to a steel bomb and was heated in an autoclave at 90° C. for 16 hours. After cooling the bomb and removing the solvent in vacuum, a yellow oil remains. The hydrochloride was prepared and recrystallized from aceton-ether to afford the title compound as a hydrochloride. Mp. 108°–109° C. Yield 5.6 g (56%).

PHARMACOLOGICAL METHODS

A. Biochemical tests

1. Inhibition of the uptake of carbon-14 5-HT and tritiated noradrenaline in vitro and in vivo The method is described by Ross, Renyi and Ögren in European Journal of Pharmacology 17 (1972), 107–112. Tricyclic antidepressant drugs of type imipramine given *in vivo* to mice decrease the uptake of $^{14}$C-5-HT and $^3$H-NA *in vitro*. The drugs were administered intraperitoneally half an hour before the animals were killed and the midbrain was taken out and sliced and incubated in a mixture consisting of, per 100 mg of brain slices, 0.2 n-mole of $^{14}C—5—HT$, 0.2 n-mole of $^3H—NA$ and 11 μmole of glucose in 2 ml of Krebs-Henseleit buffer, pH 7.4. The incubation time was 5 minutes. The radioactive amines taken up in the slices were dissolved in Soluene-350 ®(Packard) and the amounts were determined with the double labelling technique by liquid scintillation. The dose producing 50 percent decrease of the active uptake ($ED_{50}$) was determined graphically from dose response curves. Active uptake is defined as that part of the radioactive uptake which is inhibited by a high concentration of cocaine. All doses were given at least to four animals.

B. Pharmacological tests

1. 5-HTP response potentiation test

Inhibition of the uptake of 5-HT potentiates the effects of administered 5-hydroxytryptophan (5-HTP) probably by increasing the amount of 5-HT at the receptor. Three mice are given the test drugs one hour (or 4, 24 hours) before dl-5-HTP 90 mg/kg i.v. 5-HTP alone gives only a weak behavioural syndrome but in pretreated mice there is seen a characteristic behavioural syndrome, which comes within five minutes: tremor, lordosis, abduction of the hindlegs, head-twiches. The strength of the syndrome is scored from 0 to +3. Each group consists of 3 animals and at least 4 groups were tested at 25 mg/kg i.p. Control groups receiving imipramine (Tofranil®) are used as reference, since imipramine constantly potentiated dl-5-HTP. The least dose of the test compound producing maximal score (+3) in all animals is estimated from a logarithmic dose-response curve, and is denoted "effective dose" in the following Table.

DRUG INDUCED ARRHYTHMIAS IN RATS

Test drugs were intravenously administered to male rats anesthetized with Nembutal®. The doses were increased stepwise up to the lethal dose and the first dose which induced arrhythmia was noted.

ACUTE TOXICITY, BEHAVIOUR AND ANTICHOLINERGIC STUDY IN MICE

The compounds were given by intravenous route to 6 mice. $LD_{50}$ is the dose which kills 50% of the animals within 7 days. Seizures, gait, sedation and gripstrength were recorded. Pupil width (mydriasis) which reveals peripheral anticholinergic action was measured in greenlight.

The results from the above described tests are summarized in the following Table. The code numbers for the tested compounds in the Table relate to some representative compounds according to the invention which are enumerated with code numbers in the first part of this specification. All compounds according to the invention were tested in the form of their salts with hydrochloric or hydrobromic acid

TABLE

| Compound | Inhibition (50%) of uptake in vivo 5-HT[1] mg/kg i.p. | NA[2] | Potentiation of 5-HTP[3] effective dose (mg/kg i.p.) | Acute toxicity $LD_{50}$ mg/kg i.v. | Arrhythmia, accumulated i.v. dose where there are signs of arrhythmia mg/kg i.v. |
|---|---|---|---|---|---|
| GEA 654 | 15 | >40 | 1 | 70 | 63 |
| GEA 699 | 15 | >40 | 7 | — | — |
| GEA 916 | 15 | >40 | 8 | — | — |
| GEA 917 | 25 | >40 | 5 | — | — |
| GEA 935 | 5 | >40 | 3 | — | — |
| GEA 937 | 10 | >40 | 12 | — | — |
| GEA 822 | 30 | >40 | — | — | — |
| Imipramine | 24 | 6 | 15 | 28 | 8 |

[1] 5-HT = 5-hydroxytryptamine, $1 \times 10^{-7}$M
[2] NA = 1-noradrenaline, $1 \times 10^{-7}$M
[3] 5-HTP = 5-Hydroxytryptophan
i.p. = intraperitoneal administration
i.v. = intravenous administration

EVALUATION OF THE RESULTS OBTAINED IN THE PHARMACOLOGICAL TESTS

The compounds of the invention block the uptake of 5-hydroxytryptamine in brain slices in vivo but do not inhibit the uptake of noradrenaline. In vivo they are more potent than imipramine as inhibitors of the 5-hydroxytryptamine. They potentiate the responses of 5-hydroxytryptophan at considerably lower doses than imipramine. The intravenous toxicity for one tested compound is considerably lower than that of imipramine. The peripheral anticholinergic effect was found to be equal or less than that of imipramine. The heart toxicity is much weaker than that of imipramine.

These results indicate that the new compounds are much more selective than imipramine in inhibiting the uptake of 5-hydroxytryptamine in the brain of mammals, including humans, and that the unwanted side effects are considerably weaker than those of imipramine.

PHARMACEUTICAL COMPOSITIONS

The following examples illustrates the preparation of pharmaceutical compositions according to the invention. For the preparation of tablets the following compositions were made (a) 2-Aminopropanoic acid 1-(4-chlorophenyl)-2-methyl-2-propylester hydrochloride (GEA 654)   50 g
Lactose   85 g
Potatoe starch   40 g
Polyvinylpyrrolidone   5 g
Cellulose Avicel   18 g
Magnesium stearate   2 g (b) 2-Aminopropanoic acid 1-(4-chlorophenyl)-2-methyl-2-propylester hydrochloride (GEA 654)   100 g
Lactose   90 g
Potatoe starch   50 g
Polyvinylpyrrolidone   5 g
Cellulose Avicel   23 g
Magnesium stearate   2 g From the above compositions 1000 tablets were made, containing 50 mg and 100 mg of active substance, respectively. If desired, the obtained tablets can be film coated with e.g. methyl cellulose in an organic solvent.

We claim:

1. A compound of the formula

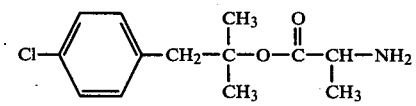

or a pharmaceutically acceptable acid-addition salt thereof.

2. A compound of the formula

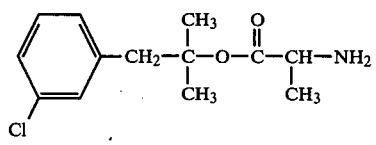

or a pharmaceutically acceptable acid-addition salt thereof.

3. A compound of the formula

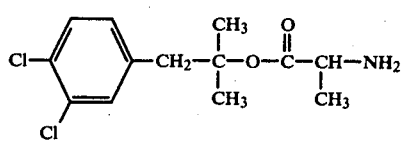
or a pharmaceutically acceptable acid-addition salt thereof.
4. A compound of the formula
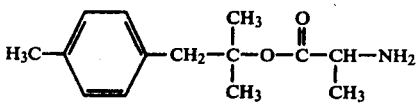
or a pharmaceutically acceptable acid-addition salt thereof.
5. A compound of the formula
H₃C—⟨phenyl⟩—CH₂—C(CH₃)(CH₃)—O—C(=O)—CH(CH₃)—NH₂
or a pharmaceutically acceptable acid-addition salt thereof.
* * * * *